(12) United States Patent
Fan et al.

(10) Patent No.: US 10,073,011 B2
(45) Date of Patent: Sep. 11, 2018

(54) MICROTOME HAVING MEANS FOR REVERSING A DIRECTION OF ROTATION

(71) Applicant: Leica Microsystems Ltd. Shanghai, Shanghai (CN)

(72) Inventors: Zheguang Fan, Shanghai (CN); Xiao Zhou, Shanghai (CN)

(73) Assignee: Leica Microsystems Ltd. Shanghai, Shanghai (CN)

( * ) Notice: Subject to any disclaimer, the term of this patent is extended or adjusted under 35 U.S.C. 154(b) by 258 days.

(21) Appl. No.: 14/287,002

(22) Filed: May 24, 2014

(65) Prior Publication Data

US 2015/0047464 A1   Feb. 19, 2015

(30) Foreign Application Priority Data

Aug. 19, 2013  (CN) .......................... 2013 1 0363047

(51) Int. Cl.

| | |
|---|---|
| *G01N 1/06* | (2006.01) |
| *F16H 3/40* | (2006.01) |
| *F16H 1/20* | (2006.01) |
| *F16H 3/34* | (2006.01) |

(52) U.S. Cl.
CPC .................. *G01N 1/06* (2013.01); *F16H 1/20* (2013.01); *F16H 3/34* (2013.01); *F16H 3/40* (2013.01); *G01N 2001/065* (2013.01); *Y10T 74/19172* (2015.01)

(58) Field of Classification Search
CPC .... F16H 1/20; F16H 3/34; F16H 3/40; G01N 2001/065

USPC ........................................................ 74/810.1
See application file for complete search history.

(56) References Cited

U.S. PATENT DOCUMENTS

| 1,736,064 | A |  | 11/1929 | Walker | |
|---|---|---|---|---|---|
| 2,506,562 | A |  | 5/1950 | Wait | |
| 2,828,648 | A |  | 4/1958 | Hazard | |
| 4,669,333 | A | * | 6/1987 | Matsuda | ................ F16H 3/003 74/352 |
| 5,249,587 | A | * | 10/1993 | Luckado | ............ B41F 13/0008 131/284 |
| 2008/0000339 | A1 | * | 1/2008 | Schneider | ................ G01N 1/06 83/703 |

(Continued)

FOREIGN PATENT DOCUMENTS

CH          233899          11/1944

*Primary Examiner* — Sean Michalski
*Assistant Examiner* — Fernando Ayala
(74) *Attorney, Agent, or Firm* — Hodgson Russ LLP

(57) ABSTRACT

A microtome has first and second shafts at different fixed positions, wherein the first shaft may be rotated by a hand wheel. The shafts carry first and second gear wheels, respectively. A transmission unit couples the two gear wheels to each other so that the second shaft can be driven to rotate by the first shaft, and a shift unit for pivotably shifting the transmission unit between first and second positions. The two shafts rotate in the same direction when the transmission unit is in the first position, and in opposite directions when the transmission unit is in the second position. The transmission unit includes first and second idler gears meshing constantly with each other. The two shafts are coupled by only one of the idler gears when the transmission unit is in the first position, and by both idler gears when the transmission unit is in the second position.

10 Claims, 4 Drawing Sheets

(56) References Cited

U.S. PATENT DOCUMENTS

2010/0263481 A1* 10/2010 Klein .................... B41J 13/103
74/810.1
2012/0060664 A1* 3/2012 Ha ......................... G01N 1/06
83/591
2015/0301492 A1* 10/2015 Ochi ................. G03G 15/6529
271/225

* cited by examiner

MICROTOME HAVING MEANS FOR REVERSING A DIRECTION OF ROTATION

CROSS REFERENCE TO RELATED APPLICATIONS

This application claims priority of Chinese patent application number 201310363047.X filed Aug. 19, 2013, the entire disclosure of which is incorporated by reference herein.

FIELD OF THE INVENTION

The present invention relates to a microtome which is manually drivable by at least one hand wheel to cut thin sections.

BACKGROUND OF THE INVENTION

Microtomes are used to cut thin sections from samples. These sections are subsequently placed on a coverslip, suitably processed, and then examined under a microscope.

Microtomes are used to cut thin sections from samples. These sections are subsequently placed on a coverslip, suitably processed, and then examined under a microscope.

In known rotary microtomes, the cutting unit is driven by turning at least one hand wheel. There are users who find it more comfortable to turn the first hand wheel clockwise, while other users find it comfortable to turn the first hand wheel counterclockwise. Therefore, there are commercially available microtomes in which the hand wheel has to be rotated clockwise, as well as microtomes in which the hand wheel has to be rotated counterclockwise. The user must choose one of the two variants at the time of purchase. The direction of rotation can later be changed only by a technician making extensive and complex modifications to the microtome.

US2008/0000339 describes a crank drive system of a shaft of a microtome. This crank drive system has the problem that in order to change the direction of rotation, the second shaft has to be moved axially together with the transfer means mounted thereon. It is also problematic that the crank drive system is complex and requires a considerable amount of space.

US2012/0060664 discloses a microtome having means for reversing a direction of rotation. The microtome comprises a first shaft which is arranged in a fixed position and capable of being driven by a hand wheel and which has a first gear wheel non-rotatably mounted thereon. The microtome further includes a second shaft which is arranged in a fixed position and has a second gear wheel mounted thereon. The first gear wheel and the second gear wheel are coupled to each other via a transmission unit, so that the second shaft can be driven by the first shaft. In a first position of the transmission unit, the two shafts are rotatable in the same direction, while in a second position of the transmission unit, they are rotatable in opposite directions. The disadvantage of the prior art is that it requires at least three idler gears for the transmission unit. This increases the complexity of the transmission unit, and requires more parts thereby increasing costs.

SUMMARY OF THE INVENTION

It is an object of the present invention to provide a microtome that is simpler, more compact and lower cost. This object is achieved by a microtome having the features described herein.

The present invention provides a microtome comprising: a first shaft which is arranged in a fixed position and capable of being driven by a hand wheel; a first gear wheel non-rotatably mounted on the first shaft; a second shaft arranged in another fixed position; a second gear wheel non-rotatably mounted on the second shaft; a transmission unit via which the first gear wheel and the second gear wheel are coupled to each other so that the second shaft can be driven by the first shaft; and a shift unit for pivotably shifting the transmission unit between a first position and a second position, wherein the first shaft and the second shaft are rotatable in the same direction when the transmission unit is in the first position, and the first shaft and the second shaft are rotatable in opposite directions when the transmission unit is in the second position, and wherein the transmission unit includes a first idler gear and a second idler gear which meshes constantly with each other, in the first position, the first shaft and the second shaft are coupled by only one of the idler gears, and in the second position, the first shaft and the second shaft are coupled by both of the idler gears.

In accordance with the present invention, the transmission unit can be pivotably shifted between a first position where the two shafts can be coupled by only one idler gear and a second position where the two shafts can be coupled by two idler gears.

By providing the transmission unit, the direction in which the hand wheel has to be rotated can be easily adapted to the preferences of an individual user by pivotably or rotatably shifting the transmission unit between its two positions. Thus, one and the same microtome can be used by several users, and the hand wheel can be operated by each user according to his or her personal preferences.

With this invention, neither the first nor the second shaft, or any other elements mounted thereon, need to be moved in order to change the direction of rotation, but may be arranged in a fixed position. As compared with the prior art, a simpler, more compact and lower-cost design is achieved. In particular, since the transmission unit is arranged in a rotatable manner, there is no need to provide a complex sliding mechanism, and it allows for fewer parts, thereby realizing a notable cost saving.

Preferably, the shift unit comprises a lever member which is pivotable at a first end thereof and is rotatably connected to the first idler gear and the second idler gear at a second end thereof.

Preferably, the lever member is rotatably connected to the first shaft at the first end and is pivotable therearound.

Preferably, the first end of the lever member is rotatably connected to one of the following: first gear wheel, the second gear wheel, the second shaft and a frame of the microtome.

Preferably, the shifting unit further comprises an actuating member which engages with the lever member.

Preferably, the actuating member is a cam or an eccentric pin.

Preferably, one axial end of the actuating member is positioned outside the housing of the microtome thereby being easily operated by a user, and the other axial end of the actuating member is positioned within a groove of the lever member thereby being engaged with the lever member.

Preferably, the actuating member is manually operable, at least a portion of which is located outside of a housing of the microtome.

Preferably, the transmission unit can be shifted manually between its first and second positions by the shift unit.

Preferably, it further comprises a spring for holding the transmission unit in its first and second positions.

The microtome is, in particular, a rotary microtome which preferably includes a first hand wheel for coarse feeding of the sample and a second hand wheel for producing the cutting motion. The hand wheel according to the present invention is used as the first hand wheel for coarse feeding of the sample.

Further features and advantages of the present invention will become apparent from the following description of exemplary embodiments thereof taken in conjunction with the accompanying drawings, in which:

DETAILED DESCRIPTION OF THE INVENTION

Figure 1:
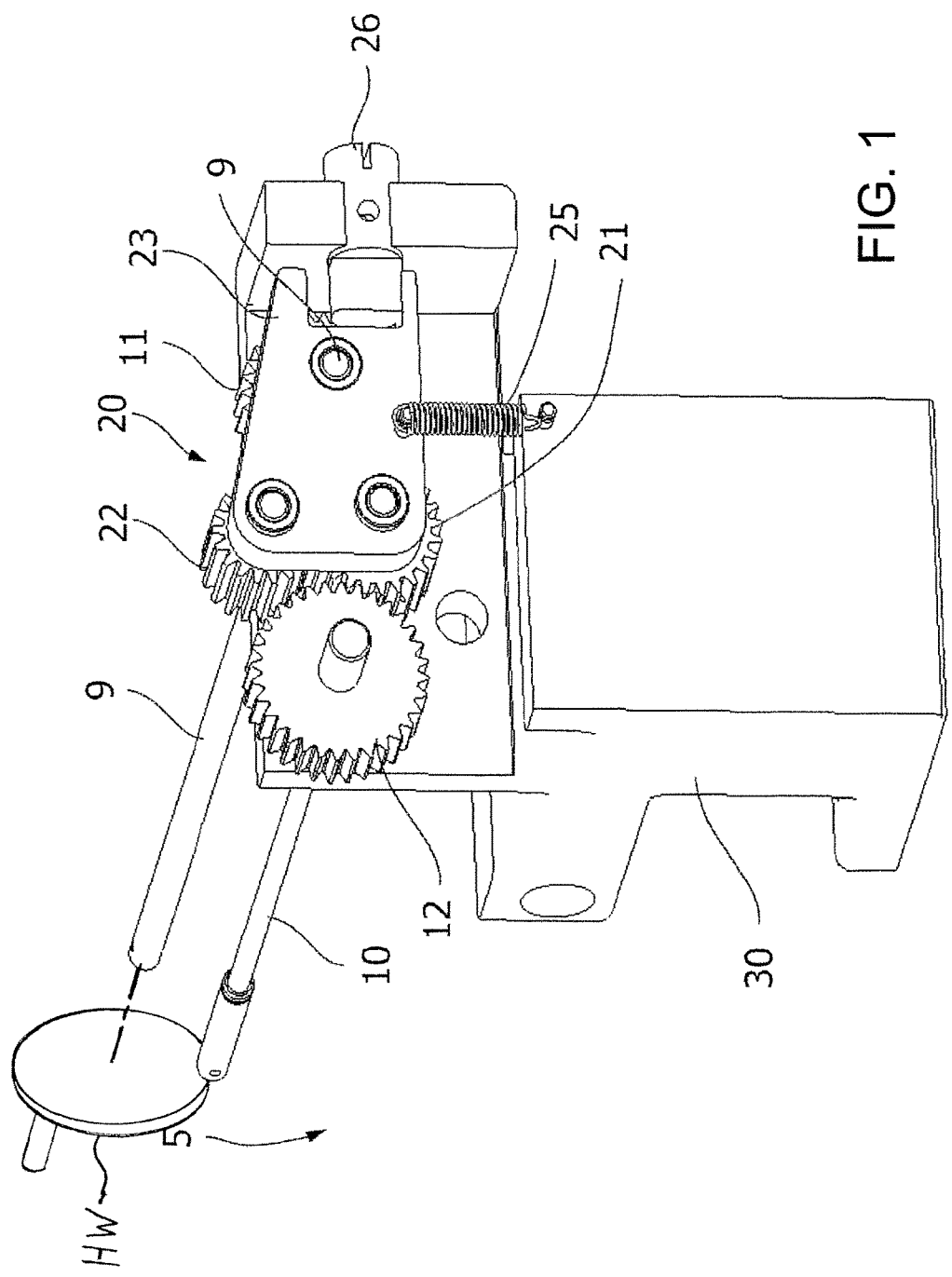
FIG. 1 is a schematic perspective view of a microtome according to a preferred embodiment of the present invention.
Figure 2:
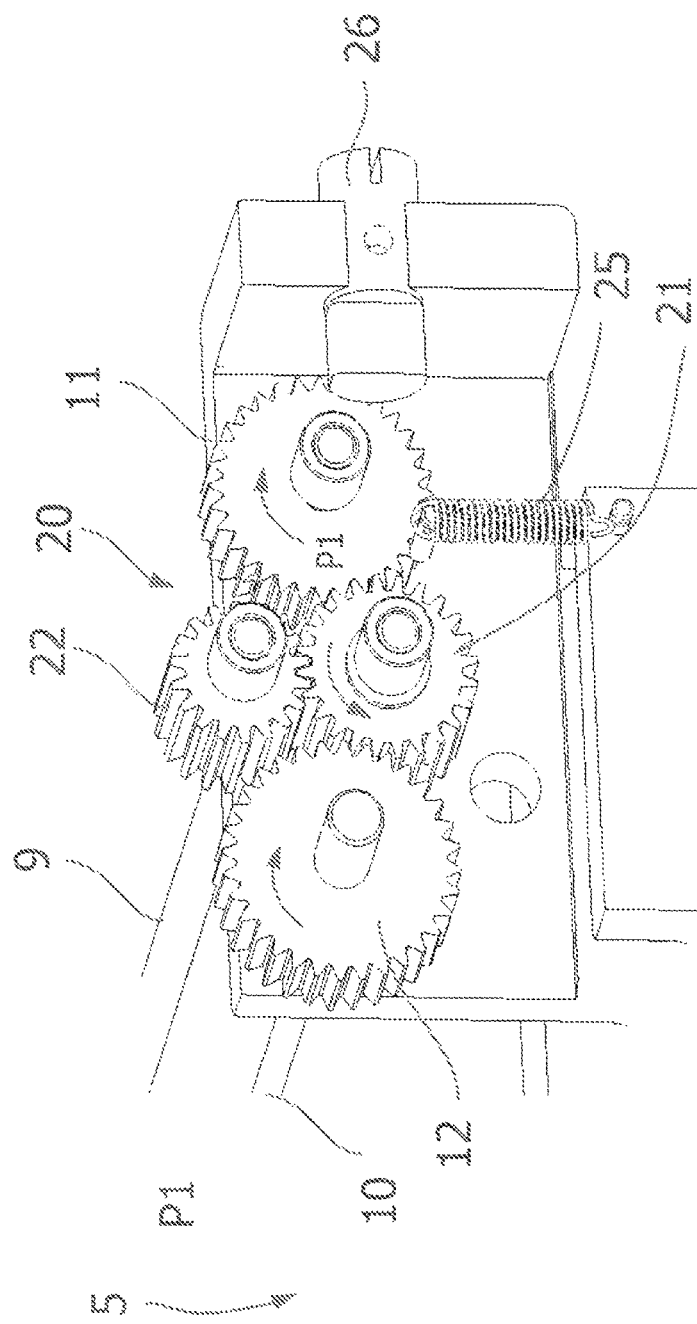
FIG. 2 is a perspective view showing the details of the transmission unit in a first transmission position, with the lever member removed to show the gear wheels.
Figure 3:
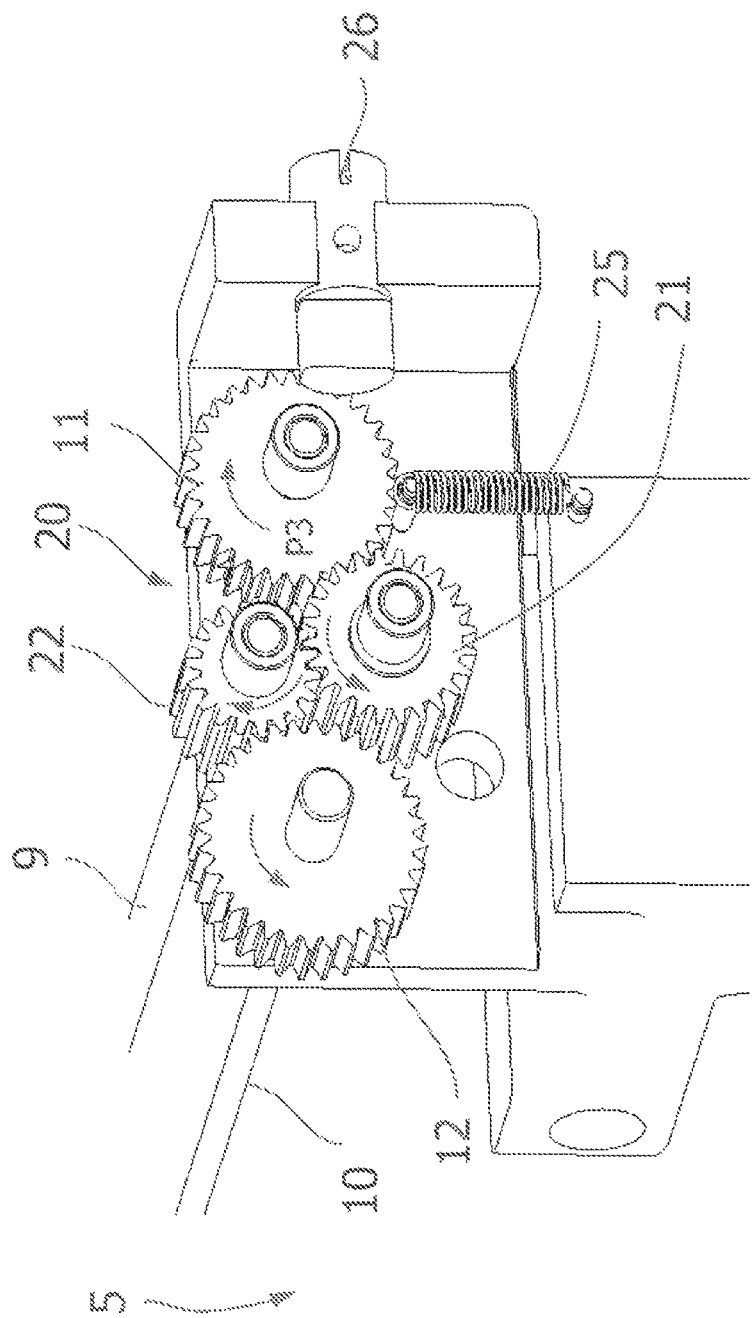
FIG. 3 is a perspective view showing the details of the transmission unit in a second transmission position, with the lever member removed to show the gear wheels.

Referring to FIG. 1, there is shown a detail of a microtome 10 in a schematic perspective view. FIG. 2 shows the transmission unit in a first position, and FIG. 3 shows the transmission unit in a second position.

Referring to FIG. 1, the microtome 5 includes a first shaft 9 having a first gear wheel 11 non-rotatably connected thereto at one end thereof. The first shaft 9 is drivable directly or indirectly by a hand wheel HW. This hand wheel may be a hand wheel for coarse feeding of the sample.

Further, the microtome 5 includes a second shaft 10 having a second gear wheel 12 non-rotatably mounted thereon at one end thereof. The second shaft 10 is accordingly used to effect coarse feeding and/or to produce the cutting motion. The cutting unit is not shown in FIGS. 1 through 3. The shafts 9, 10 are mounted via bearing units (not shown) in a frame 30. The two shafts 9, 10 and the gear wheels 11, 12 mounted thereon are arranged in fixed positions relative to the frame of the microtome 5.

The gear wheels 11, 12 can be coupled to each other via a transmission unit 20, so that the second shaft 10 can be driven by the first shaft 9. This allows the second shaft 10 to be driven by the hand wheel, so that the motion as required can be produced by rotating the hand wheel.

The transmission unit 20 is shiftable between a first transmission position and a second transmission position. In FIG. 2, the transmission unit 20 is shown in its first position. The transmission unit 20 includes a first idler gear 21 and a second idler gear 22 which meshes constantly with each other. When the transmission unit 20 is in the first position, the first idler gear 21 is in meshing engagement with both the first gear wheel 11 and the second gear wheel 12, so that the two gear wheels 11, 12 are coupled to each other via only one idler gear, i.e., the first idler gear 21.

When the first shaft 9 is rotated as indicated by arrow P1 in FIG. 2, the first gear wheel 11 is rotated in the same direction. The first idler gear 21 is rotated in a direction opposite to that of the first shaft 9. The first idler gear 21 in turn drives the second gear wheel 12 to rotate in the same direction as the first shaft 9. Since the second gear wheel 12 is non-rotatably connected to the second shaft 10, the second shaft is rotated in the same direction as P1. Accordingly, the first shaft 9 and second shaft 10 are driven in the same direction of rotation.

When the first shaft 9 is rotated in a direction opposite to arrow P1, the second shaft 10 is also rotated in a direction opposite to the arrow P1. That is, the first shaft 9 and the second shaft 10 are also driven in the same direction of rotation.

Figure 4:
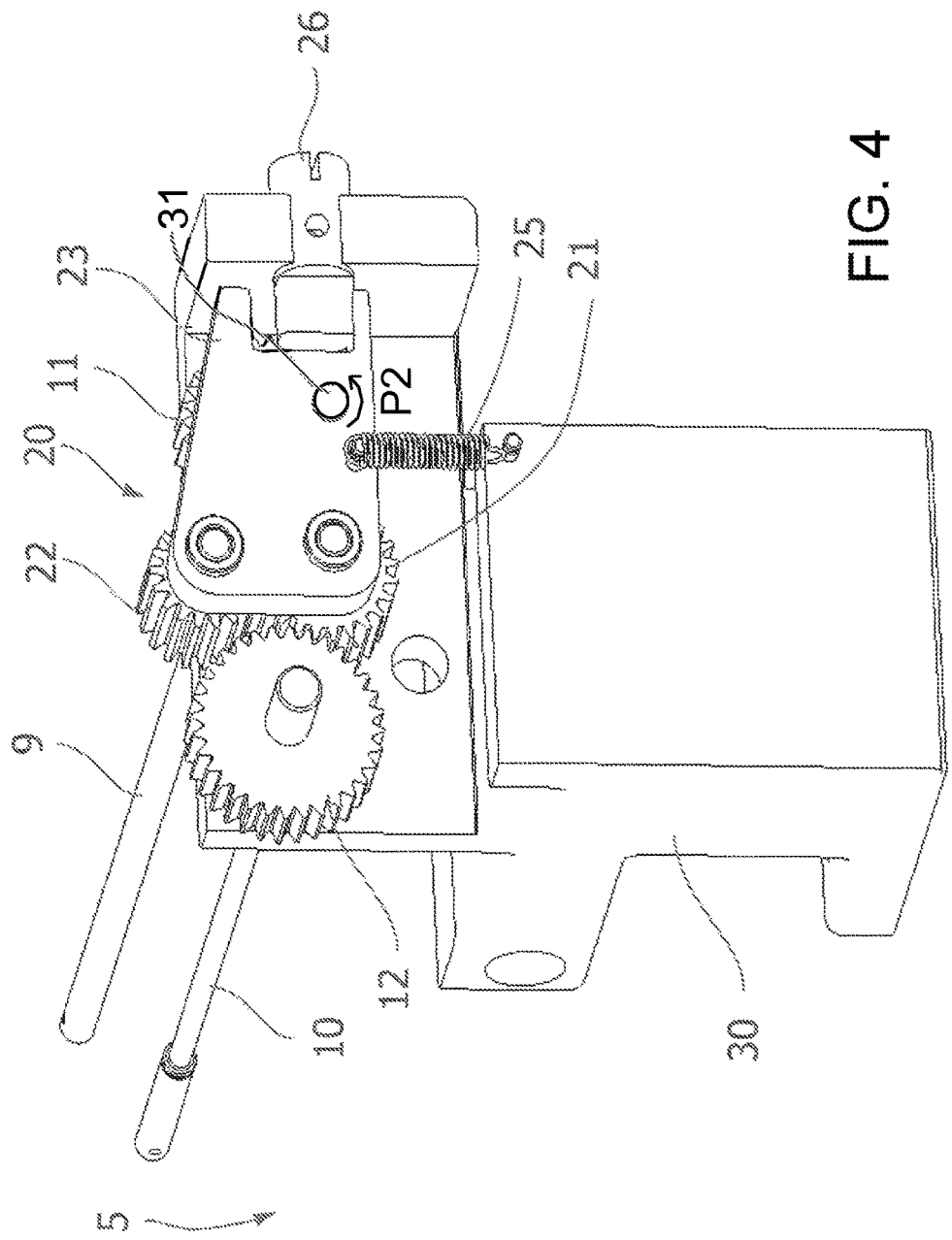
FIG. 4 is a schematic perspective view of a microtome according to an alternative embodiment of the present invention.

A shifting unit allows the transmission unit 20 to be manually shifted between the first transmission position and the second transmission position. The shift unit comprises a lever member 23 which is pivotable at a first end thereof and is rotatably or pivotably connected to the first idler gear 21 and the second idler gear 22 at a second end thereof. In this embodiment, the lever member 23 is rotatably or pivotably connected to the first shaft 9 at the first end and is pivotable therearound. However, it should be appreciated that the first end of the lever member 23 can be connected to other positions, for example, the first gear wheel 11, the second gear wheel 12, the second shaft 10, or the frame 30. See, for example, the alternative embodiment shown in FIG. 4 wherein the first end of lever member 23 is pivotably connected to frame 30 at pivot pin 31.

Preferably, the shifting unit further comprises an actuating member 26, for example, a cam or an eccentric pin, at least a portion of which is located outside of the housing of the microtome 5. The actuating member 26 is provided to engage with the lever member 23. In particular, one axial end of the actuating member 26 is positioned outside the housing of the microtome 5 thereby being easily operated by a user, and the other axial end of the actuating member 26 is positioned within a groove of the lever member 23 thereby being engaged with the lever member 23. It should be appreciated that, in addition to a cam or an eccentric member, the actuating member 26 can be of other form, for example, an operating member that is connected to the lever member 23 and can be translationally moved in a groove in the housing so that it enables the lever member 23 to pivot.

When the transmission unit 20 is in its first or second position, the actuating member 26 engages with a latching member, causing the transmission unit to be retained in the respective position and preventing unintensional shifting between the transmission positions.

Preferably, a spring 25 is provided to hold the transmission unit 20 in its first and second positions. Preferably, the spring is connected to the lever 23 at one end thereof, and is connected to the frame 30 at the other end thereof. In order to shift the transmission unit 20 from its first to its second position or vice versa, the transmission unit 20 is moved against the force of the spring 25.

In this embodiment, in order to shift the transmission unit 20 from its first position (FIG. 2) to its second position (FIG. 3), the actuating member (cam) 26 can be rotated by a user manually, for example, by 90 degrees, then the lever member 23 is pivoted or rotated around the first shaft 9 so that the transmission unit 20, including the first idler gear 21 and the second idler gear 22, is pivoted by a certain angle counter clockwise (as shown in FIG. 1, arrow P2) and is shifted to the second position, which is shown in FIG. 3. In the second transmission position, the second idler gear 22 is in meshing with the second gear wheel 12, and meanwhile, the first idler gear 21 disengages with the second gear wheel 12. That is, there are engagements, in turn, among the first gear wheel 11, the first idler gear 21, the second idler gear 22 and the second gear wheel 12. In other words, since the first and second idler gears 21, 22 and the first gear wheel 11 are constantly in meshing, in the second position, the two gear wheels 11, 12 are coupled to each other via both of the idler gears 21, 22. In the second position, if the first shaft 9 is rotated as indicated by arrow P3 in FIG. 3, the second shaft 10 will rotate in the opposite direction, that is, the two shafts 9, 10 are rotated in opposite directions when the transmission unit 20 is in its second position.

With the present invention, the pivotable shifting of transmission unit 20 provides an easy way to select the direction in which first shaft 12, and thus also the hand wheel firmly connected thereto, must be rotated. Thus, the direction of rotation of the hand wheel can be selected by any user in accordance with what he or she feels to be more comfortable, so that microtome 5 can be used by several users, and the hand wheel for coarse feeding of the sample can be rotated by each user in his or her preferred direction.

Although the present invention has been described with respect to one or more particular embodiments, it should be understood that other embodiments of the present invention may be made without departing from the spirit and scope of the present invention.

LIST OF REFERENCE NUMERALS 5 microtome
9, 10 first and second shafts
11, 12 first and second gear wheels
20 transmission unit
21, 22 first and second idler gears
23 lever
25 spring
26 actuating member
30 frame
31 pivot pin
HW hand wheel
P1, P2, P3 direction or rotation

What is claimed is:

1. A microtome (5) comprising:
a frame (30);
a first shaft (9) arranged in a fixed position relative to the frame and capable of being driven to rotate by a hand wheel;
a first gear wheel (11) non-rotatably mounted on the first shaft for rotation with the first shaft;
a second shaft (10) arranged in another fixed position relative to the frame;
a second gear wheel (12) non-rotatably mounted on the second shaft for rotation with the second shaft;
a transmission unit (20) via which the first gear wheel (11) and the second gear wheel (12) are coupled to each other so that the second shaft (10) can be driven to rotate by rotation of the first shaft (9); and
a shift unit for pivotably shifting the transmission unit (20) between a first position and a second position, wherein the shift unit pivots the transmission unit (20) about only one axis to shift the transmission unit (20) between the first position and the second position;
wherein the first shaft (9) and the second shaft (10) are rotatable in the same direction when the transmission unit (20) is in the first position, and the first shaft (9) and the second shaft (10) are rotatable in opposite directions when the transmission unit (20) is in the second position;
wherein the transmission unit (20) includes a first idler gear (21) and a second idler gear (22) constantly meshing with each other, wherein respective rotational axes about which the first idler gear (21) and the second idler gear (22) rotate are fixed relative to the shift unit;
wherein one of the first and second idler gears (21, 22) is meshed with the first gear wheel (11) and with the second gear wheel (12) when the transmission unit (20) is in the first position, whereby the first shaft (9) and the second shaft (10) are coupled by only the one of the first and second idler gears when the transmission unit is in the first position; and
wherein the first idler gear (21) is meshed with the first gear wheel (11) and the second idler gear (22) is meshed with the second gear wheel (12) when the transmission unit (20) is in the second position, whereby the first shaft (9) and the second shaft (10) are coupled by both of the first and second idler gears when the transmission unit is in the second position.

2. The microtome (5) according to claim 1, wherein the shift unit comprises a lever member (23) which is pivotable at a first end thereof about the one axis and is rotatably connected to the first idler gear (21) and the second idler gear (22) at a second end thereof.

3. The microtome (5) according to claim 2, wherein the lever member (23) is rotatably connected to the first shaft (9) at the first end and is pivotable around the first shaft.

4. The microtome (5) according to claim 2, wherein the first end of the lever member (23) is rotatably connected to one of the following: the first gear wheel (11), the second gear wheel (12), the second shaft (10), and a frame (30) of the microtome.

5. The microtome (5) according to claim 2, wherein the shift unit further comprises an actuating member (26) engaged with the lever member (23).

6. The microtome (5) according to claim 5, wherein the actuating member (26) is a cam or an eccentric pin.

7. The microtome (5) according to claim 6, wherein one axial end of the actuating member (26) is positioned outside a housing of the microtome (5) to be operable by a user, and the other axial end of the actuating member (26) is positioned within a groove of the lever member (23) thereby being engaged with the lever member (23).

8. The microtome (5) according to claim 5, wherein the actuating member (26) is manually operable.

9. The microtome (5) according to claim 1, wherein the transmission unit (20) can be shifted manually between its first and second positions by the shift unit.

10. The microtome (5) according to claim 5, further comprising a spring (25) biasing the lever member (23) toward engagement with the actuating member (26) for holding the transmission unit (20) in its first and second positions, respectively.

* * * * *